United States Patent [19]

de Wit et al.

[11] Patent Number: 4,529,949
[45] Date of Patent: Jul. 16, 1985

[54] BIAS CONTROL CIRCUIT FOR LIGHT-EMITTING DIODE HAVING TEMPERATURE COMPENSATION

[75] Inventors: Benjamino de Wit, Kerk Avezaath; Karel H. Wesseling, Bunnik, both of Netherlands

[73] Assignee: Nederlandse Centrale Organisatie voor Toegepast-Natuurwetenschappelijk Onderzoek, The Hague, Netherlands

[21] Appl. No.: 465,190

[22] Filed: Feb. 8, 1983

[30] Foreign Application Priority Data

Feb. 11, 1982 [NL] Netherlands ................... 8200517

[51] Int. Cl.$^3$ ............................................. H03F 3/04
[52] U.S. Cl. ..................................... 330/289; 330/296
[58] Field of Search ............... 330/289, 296, 59; 357/28; 307/310

[56] References Cited

U.S. PATENT DOCUMENTS 3,686,517 8/1972 Sexton ................................. 330/289

FOREIGN PATENT DOCUMENTS 2309446 8/1974 Fed. Rep. of Germany .
8004071 2/1982 Netherlands .

Primary Examiner—James B. Mullins
Assistant Examiner—G. Wan
Attorney, Agent, or Firm—Cushman, Darby & Cushman

[57] ABSTRACT

A bias control circuit for a light-emitting diode having compensation of the light output at changing temperature, in which the light-emitting diode (led) used as temperature sensor is taken up together with a series resistor (R3) in a series circuit to which a fixed supply voltage is applied. A further series circuit of two resistors (R1, R2) having strongly different values is connected parallel across the series resistor (R3) and a differential amplifier (A1) is provided, the one and the other input of which are connected respectively to the junction of the two resistors (R1, R2) and to a setting voltage (Vi), and the output of which is connected to a control means (Tr1) taken up in series with the one series circuit.

8 Claims, 8 Drawing Figures

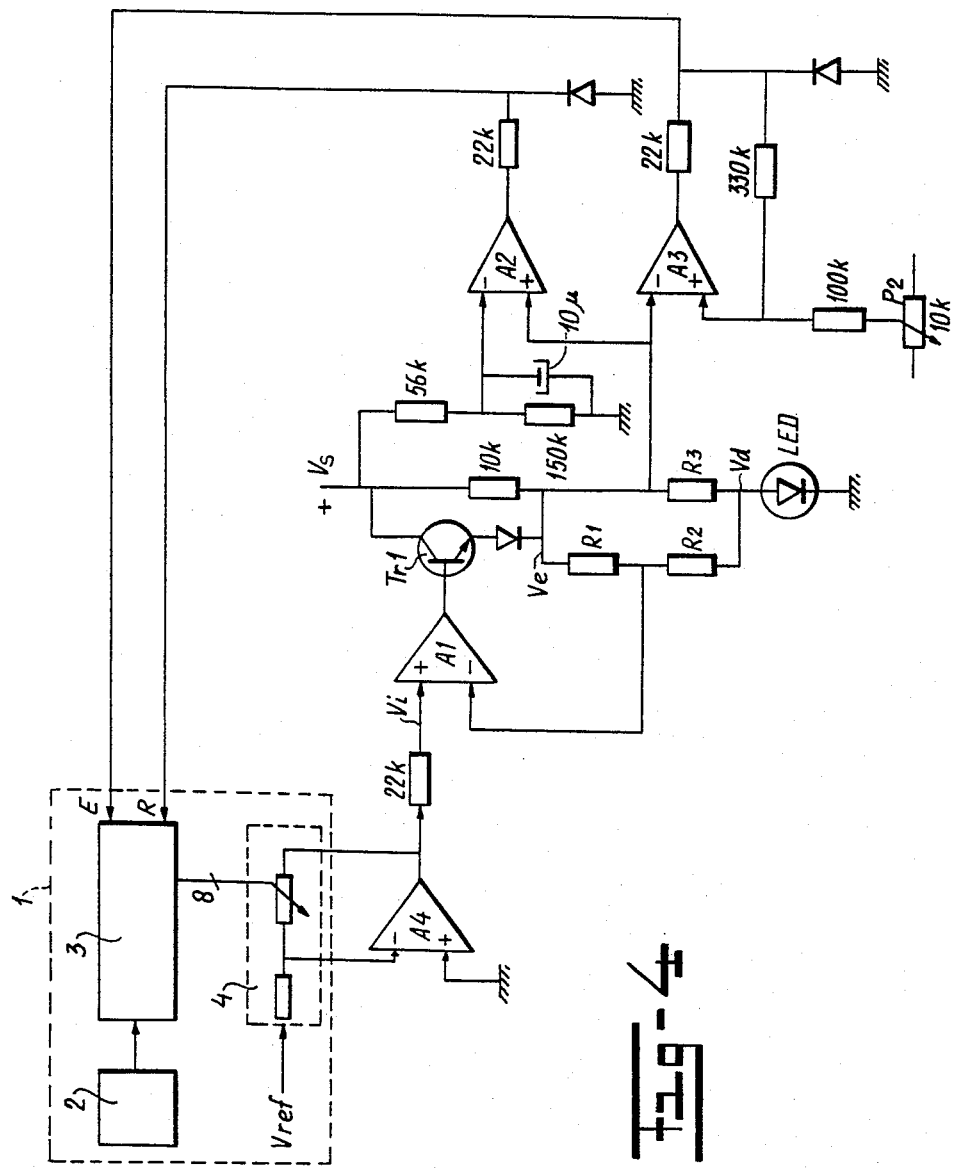

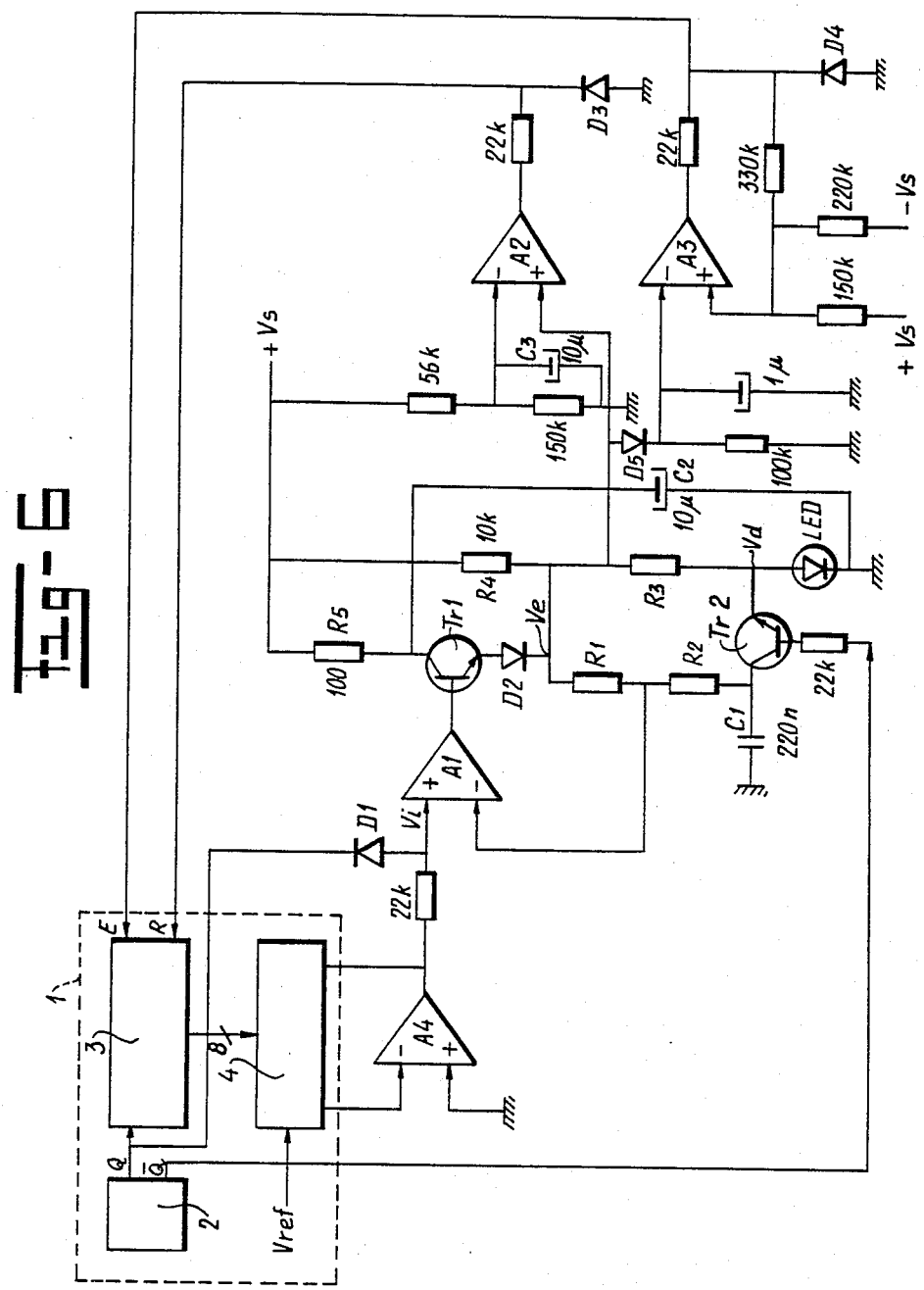

BIAS CONTROL CIRCUIT FOR LIGHT-EMITTING DIODE HAVING TEMPERATURE COMPENSATION

BACKGROUND OF THE INVENTION

The invention relates to a bias control circuit for a light-emiting diode having compensation of the light output at changing temperature, in which the light-emitting diode (led) per se is used as temperature sensor and is taken up together with a series resistor in a series circuit to which a fixed supply voltage is applied. Such a bias control circuit is known from the German Offenlegungsschrift No. 2,309,446.

When an electric current is passed through a light-emitting diode, this diode will emit a visible or infrared light radiation. The amount of light or light output of the diode depends on the magnitude of the current and on the temperature of the diode. So, the light output will decrease at increasing temperature of the surroundings and vice versa. Also the central wavelength and the band width of the light emitted by the diode will change slightly with temperature. This is, however, less important when the photodetector or photocell, cooperating with a led, which will detect the light, has a sufficiently wide spectral sensitivity.

This dependency on temperature in applications including digital or FM-modulated circuits, is less essential as in these circuits mainly the presence or absence of light or the frequency of the light intensity modulation respectively is detected. However, in applications including analog or proportional circuits the amount of light indeed is essential and the dependency of temperature has to be taken into account.

The bias control circuit of above mentioned Offenlegungsschrift is limited herein, that the resistance value in this circuit is attuned to the light-emitting diode used in accordance with a specific equation. When changing one led for another having mutually different characteristics, the resistance value in this circuit has to be adjusted according to said equation.

In an other bias control circuit known from Netherlands Patent Application No. 80.04071, which has compensation of the light output at changing temperature, apart from a first photodetector cooperating with the led for certain applications, an identical second photodetector as a separate temperature sensor is used. Thereby, besides the amount of light which is transmitted via the object, to be measured, between the led and the first photodetector, also a specified amount of light is transmitted directly to the second photodetector. This second detector together with an amplifier and a control means, connected in series with the diode, is taken up in a control loop to compensate the current through the diode when temperature varies.

The second photodetector required for this known bias control circuit makes this circuit clumsy and even useless, when in certain applications there is only very limited space available for mounting the led and both photodetectors, such as for example in an inflatable cuff having a light plethysmograph.

SUMMARY OF THE INVENTION

The object of the invention is to obviate the above problems and to provide a bias control circuit for a light-emitting diode having compensation of the light output, which bias control circuit is of a simple and cheap construction and is small-sized as well. According to the invention this is attained with a bias control circuit of the type mentioned in the preamble in that a further series circuit of two further resistors is connected parallel across the series resistor in the one series circuit and that a differential amplifier is provided, the one and the other input of which are connected respectively to the junction of the two further resistors and to a setting voltage and the output of which is connected to a control means taken up in series with the one series circuit. In this embodiment the led itself, viz. the forward voltage over the led is used to advantage as temperature sensor. The temperature at the led is determined from its own forward voltage, which voltage determines the current through the led.

By giving said two further resistors in the further series circuit mutually different values a lever circuit is obtained having unequal resistance arms, the hinged point of which is formed by the differential amplifier.

In an additional further advantageous embodiment of the bias control circuit of the invention, the light emission of the led is modulated. In this embodiment the somewhat disturbing effect can be obviated which comes about as the forward voltage of the led when conducting is dependent not only on the temperature but also on the diode current which varies due to temperature compensation. Said temperature compensation in the on-period of the led is now realized solely on the basis of the forward voltage in the off-period, which voltage itself is determined by the led temperature, and the constant rest current flowing in said off-period.

Such a bias control circuit can be applied to advantage in a light plethysmograph. Hereby, the light which is emitted by the led in constant quantity, is detected, after a partial interception of same by absorbing or dispersing tissue, by a photodetector connected to a proportional circuit. The amount of detected light, in this case, is essential.

BRIEF DESCRIPTION OF THE DRAWINGS

The invention will be explained in detail on the basis of some embodiments with reference to the drawings, in which

FIG. 4 shows a diagram of another further embodiment of the bias control circuit according to the invention having automatic adjustment;

FIG. 6 shows a diagram of still a further embodiment of the bias control circuit according to the invention.

DETAILED DESCRIPTION OF THE INVENTION

Figure 1:
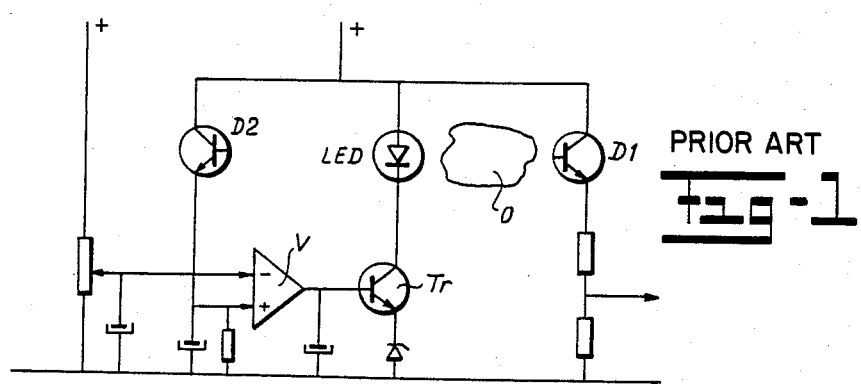
FIG. 1 shows a diagram of a known bias control circuit.

FIG. 1 shows a bias control circuit known from Netherlands Patent Application No. 80.04071. The light emitted by the led is transmitted via the object O to be measured to the photodetector D1. The output signal of said photodetector is derived via a voltage divider for further processing. The light emitted by the led is also transmitted directly to a second photodetector D2. The output signal of D2 is supplied to an input of a differential amplifier V, the other input of which is connected to a setting voltage. The output signal of the differential amplifier V is used, by means of the control transistor Tr, to adjust the current through the led in order to compensate changes in the light output of the led at changing temperature.

Figure 2:
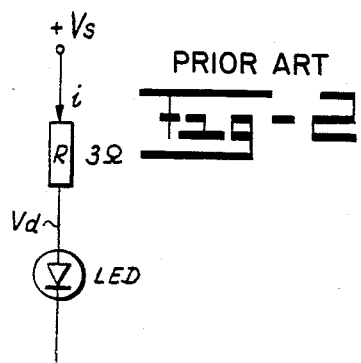
FIG. 2 shows a diagram of a series circuit to explain the temperature effect on the led in the series circuit.

FIG. 2 shows a series circuit in which a led is taken up in series with an ohmic impedance R of e.g. 3Ω, which series circuit is fed by the fixed supply voltage Vs of e.g. 1.8 V. The voltage Vd over the led is then about 1.5 V. In this series circuit the led itself is used as indicator of the changing temperature, thus a temperature sensor. The forward voltage Vd over the led decreases when temperature at the diode rises so that at fixed supply voltage Vs over the total series circuit, the voltage over the resistor increases the same amount. Consequently, the current through the series circuit increases due to which the quantity of light emitted by the diode is rightly compensated.

Measurements have shown that:

(1) at increasing temperature the quantity of light decreases practically linearly by about 0.6%/°C.;
(2) at increasing temperature the forward voltage over the diode decreases about linearly by about 1.2 mV/°C.;
(3) at increasing intensity of current i the emitted quantity of light I increases practically in direct proportion, viz. $I = i^{1.16}$; and
(4) the mutual dispersion in these values is largely a factor 10 smaller than the systematic drift, so that compensation is achieved.

The values mentioned above with regard to the components in FIG. 2 give a fair compensation of the change in quantity of light at changing temperature, when the effect of increased forward voltage over the diode at increased current intensities, required for compensation of decreased quantity of light, is not taken into account. In case this effect is taken into account, then the value of the series resistor should at least be a factor 2 smaller.

For, in general, the leds vary in forward voltage Vd for a given current, e.g. 100 mA, and light output. In case the led is connected to a fixed supply voltage of 1.5 V, then the current in one led may be 50 mA and in an other 100 or 200 mA, with which the light output varies accordingly. Therefore, leds are mostly connected via a large series resistor to a higher supply voltage. In that case supply voltage and resistor substantially determine the current. The current in case of a Vs of 6.5 V and a resistor of 50 Ohm is 100 mA at a diode voltage Vd of 1.5 V (5 V over the resistor). The current, however, in case of diode voltages Vd of 1.4 and 1.6 V, is 102 and 98 mA respectively, thus approximately the same.

Figure 3:
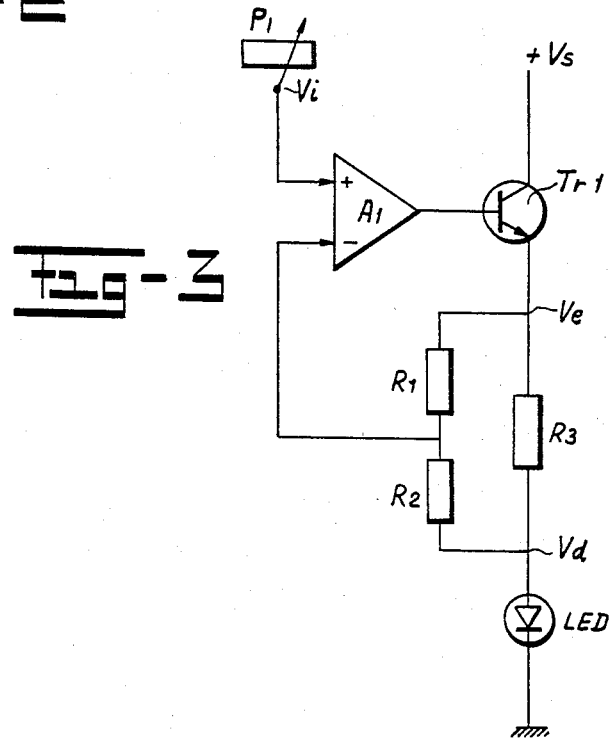
FIG. 3 shows a diagram of an embodiment of the bias control circuit according to the invention.

In order to be able to control the bias of led's having mutually different characteristics in an arrangement with higher resistance values and at higher voltages, according to the invention a bias control circuit, derived from the basic embodiment of FIG. 2, is used. In this bias control circuit shown in FIG. 3 a lever circuit having different resistor arms and as a hinged point an operational amplifier applied as comparator is used.

The led current in the series circuit traverses a larger resisor R3, of e.g. 47 Ohm, and is controlled by a higher and variable voltage Ve.

Two further resistors R1 and R2 in a further series circuit are connected parallel to the resistor R3 in the one series circuit, which resistors R1 and R2 form the unequal arms of the lever. The junction point of the two resistors is connected to the minus input of the comparator A1, the plus input of which is connected to an adjustable setting voltage Vi from the potentiometer P1. The output of the comparator A1 is connected to the control input of a control means such as a transistor Tr1. Said transistor Tr1 is taken up in series with the one series circuit and is connected to the fixed supply voltage +Vs. When the forward voltage over the led decreases due to an increase of temperature at this led, the voltage at the minus input of the comparator A1 will also decrease in dependency of the ratio of the values of R1 and R2.

The control voltage from the output of the comparator A1 for the basis of the transistor Tr1 controls this transistor such that the voltage Ve at the emitter increases. Consequently, the current through the series circuit and in the led will also increase. The emitter voltage Ve has to increase in proportion to the resistance ratio R1/R2 due to the feedback via the network, in order to cause the voltage at the minus input of the comparator A1 to be equal again to the setting voltage Vi at the plus input.

The values of the resistors in the network can be as follows: R1=200 kΩ, R2=3.9 kΩ, R3=47Ω.

The potentiometer P1 is adjusted for the supply of a setting voltage Vi such that at a given temperature the correct current is passed through the series circuit to the led in order to obtain the correct quantity of light emission. When the led is replaced, the potentiometer can be adjusted anew to get the correct Vi.

FIG. 4 shows another further embodiment of the bias control circuit according to the invention having automatic bias control of the led. This aromatic bias control of the voltage Vi for the led occurs when the supply voltage is switched on and also, when the led is inserted (again) at available supply voltage. The series circuit having the lever circuit and comparator, shown in FIG. 3, are indicated again in FIG. 4 as a network comprising the resistors R1, R2, R3, the led and the comparator A1.

In this bias control circuit the setting voltage Vi is increased stepwise from zero up to the voltage Ve being high enough for a sufficient current through the series circuit of R3 and led.

The plus input of the comparator A1 is, therefore connected to a step generator 1, which via the buffer amplifier 4 supplies at its output a stepwise changing output voltage. An input of a trigger means A3, e.g. a comparator or operational amplifier having Schmitt-effect, is connected to the resistor R3 in the series circuit. The other or plus input of this trigger means is connected to a reference voltage from the potentiometer P2. The output of the trigger means A3 is connected to an enabling input E of the step generator 1. An input of a conversion means A2, e.g. a comparator or an operational amplifier, is also connected to the resistor R3 in the series circuit. The other input of said conversion means is connected to a fixed voltage, while its output is connected to a reset input R of the step generator 1.

The step generator 1 can advantageously consist of a clock circuit 2, a binary counter 3 and a digital-to-analog converter 4. The binary counter 3 is connected via a parallel eight-bit output to the converter 4. This converter can be considered as a switchable resistor ladder network, one resistor being fixed and one being variable. One of the resistors is taken up as feedback resistor of the amplifier A4, the other resistor is connected both to the one input of A4 and to a reference voltage Vref. The fixed and the variable resistor can be exchanged. It is, however, also possible that the step generator 1 consists of another lasting stable memory.

When the supply voltage is switched on to the bias circuit and/or in case of removed led, there is initially a higher voltage at the plus input of the conversion means or comparator A2 than at its minus input. Consequently, the output of A2 is at high level and the binary counter 3 is in its reset state. The input voltage of the comparator A4 and also its output voltage Vi is zero. Further, the output of the conversion means or comparator A3 is at low or high level when the led is absent or inserted respectively.

The output of A2 will switch from high to low level when the supply voltage is now switched on or when the led is inserted at available supply voltage, so that the reset voltage at the reset input R of the counter 3 drops off. The counter 3 is now started by the enabling signal from A3 and starts counting the block pulses of the clock circuit 2. This increases the counter and the output voltage of the comparator A4 increases stepwise. Thereby also the voltage Ve increases via the comparator A1 and the lever having the unequal arms R1 and R2. This continues until the switching level of the conversion means or the comparator A3, determined by the reference voltage of P2, is reached. The enabling signal for the counter 1 then drops off, by which the counter is maintained in its reached position.

The switching level of the trigger means A3 is set for once by the potentiometer P2. At a typical frequency of 10 kHz of the clock circuit and with an eight-bit counter 3 this one-time automatical setting takes at maximum 25 seconds.

The above will be explained in further detail on the basis of a numeral example. The voltage Vi is set for once in the bias control circuit, in such a way, adapted to the forward voltage Vd of the led and approximately as large, that the voltage Ve is e.g. 6.5 V in dependence of the voltage set at P2. The current then approximates 100 mA. Thereafter small changes in Vd caused by temperature variation are amplified by A1 and the resistance ratio R1/R2 into Ve, and converted via the constant series resistor R3 into considerable current variations. The measurements (1), (2) and (3), mentioned in the explanation of FIG. 2, show roughly that a current variation of 1 mA/mV is required, which variation of 1 mA compensates for a variation of 1° C. A current variation of 1 mA requires a voltage variation in Ve of 50 mV when a resistor R3 of 50 Ohm is used, which means a voltage gain of 50 times (roughly R1/R2). The voltage Vi does not change anymore when the counter 3 is fixed after the Schmitt trigger circuit A3 is triggered once and is no longer sensitive to relatively small variations in Ve. In other words, the one time setting provides initially for a fixed value of Ve, set by P2, of e.g. 6.5 V controlled by the voltage Vi on A1.

Figure 5A:
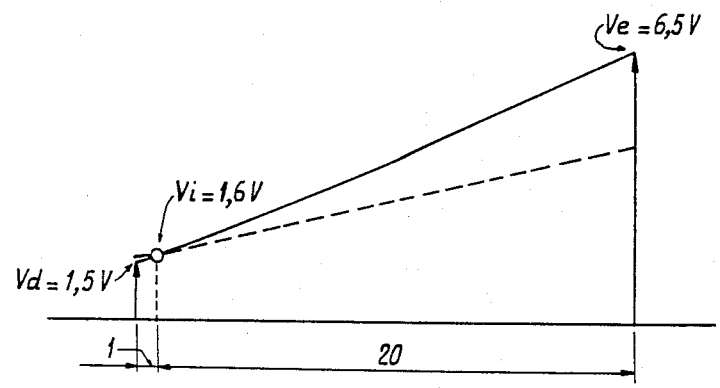
FIG. 5 shows some graphs to explain the operation of the lever circuit used in said embodiments.

FIG. 5 shows same graphs for explaining the operation of the lever circuit. FIG. 5a indicates the case of a led of which the forward voltage Vd is 1.5 V at a correct light output of the diode. Upon the initial one-time setting, Vi appears to be 1.6 V at an (initially fixed) voltage Ve of 6.5 V. After said initial setting Vi remains fixed as explained above and will function as hinged point of the lever circuit. An increase of Vd due to temperature decrease causes, via the lever operation, a much larger decrease of Ve and an associated decrease of the curent through R3 and the led in order to compensate the light output. The dotted line in FIG. 5a shows as an example how Vd and Ve can vary.

Figure 5B:
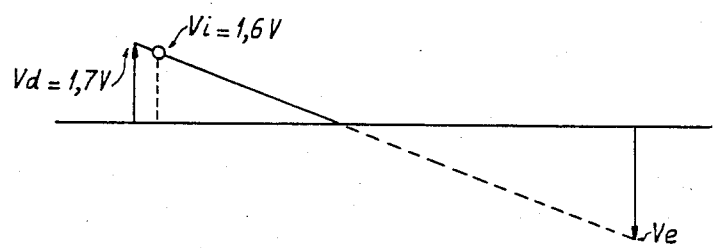

FIG. 5b shows the case that already initially Vi is set at 1.6 V for a given led having a correct light output at a forward voltage Vd of 1.7 V. The corresponding voltage of Ve in the lever circuit would have to be negative which of course is impossible. This case illustrates that Vi advantageously should be adjustable at the beginning to cope with different led's each having a differing Vd.

Figure 5C:
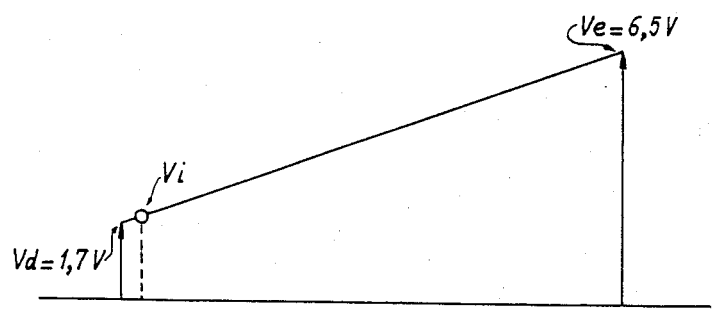

FIG. 5c shows the case of the same led as in FIG. 5b but now with an adjustable Vi. That means that, at the initial one-time setting for this led having Vd of 1.7 V, a Vi is found larger than 1.7 V at an initially fixed voltage Ve=6.5 V determined by Vi. After this initial setting Vi remains fixed.

FIG. 6 explains an additional further and improved embodiment of the bias control circuit according to the invention, which can be used for applications in which modulated light is allowed or required.

For a number of applications it may be necessary to modulate the light of the led at a relatively high frequency. The amplifier of the photodetector cooperating with the led is then tuned to the modulation frequency and becomes insensitive to supply hum of 50 Hz or 60 Hz and ambiant light having a relatively slow or fast variation in light intensity.

The modulation of the light from the led can be obtained by switching the current through the led on and off. For this purpose, the plus input of the comparator A1 is connected via a separating means, such as a diode D1, to the output Q of the clock circuit 2. The output signal of this output Q is a pulsatile signal in which pulses between zero volt and the supply voltage Vs occur with a frequency of 10 kHz.

In the period half in which the current in the series circuit comprising the led is almost switched off due to the pulsatile output signal Q, there is still a very weak residual current through the led supplied via the resistors R4 and R3. The forward voltage over the led in this period half is almost solely determined by the small constant "off" or rest current and the led temperature, and not by the "on" current changing as a result of the temperature compensation in the other period half.

A very good and stable compensation can be obtained in the other or "on period" with the aid of a switching means or transistor Tr2, which is switched in counter phase. Said transistor Tr2 is connected to the inverting output $\overline{Q}$ of the clock circuit 2. The transistor Tr2 is conductive in the "off" period of the led, and the forward voltage Vd and consequently the associated temperature is stored in the capacitor C1. For, in the "on" period the temperature compensation operates, via the lever with unequal arms R1, R2, only on the basis of the voltage stored in C1 and not on the basis also of the forward voltage Vd changing as a result of current variation, as Tr2 is not conductive in this period. The forward voltage does not depend only on temperature, but also on current, and because the latter varies as a result of the compensation, this is a somewhat disturbing effect. The disturbance is bypassed by effecting the compensation in the "on" period on the basis of the forward voltage Vd, which is determined in the "off" period at constant rest current.

The values of the resistors R1 and R2 are now changed, viz. 200 kΩ and 10.5 kΩ. The value of the resistor R3 is again 47Ω at an "on" current intensity of about 10 mA at 20° C.

The current through the led varies periodically between 1 and 100 mA. This pulsatile current must be kept as much as possible out of the remainder of the circuit. The pulsatile current component is localized in the circuit formed by Tr1, D2, R3, led and C2 by means of the resistor R5, which also decrases the dissipation in the transistor Tr1, and the capacitor C2.

The various components in the bias circuit can be of the following type. The diodes can be silicon diodes. The transistors Tr1 and Tr2 can be of the type BC109C. The comparators or operational amplifiers can be of the type LF347. The clock circuit can be a chip 4047. The binary counter can be of the type 14520. The digital-to-analog converter can be of the type AD 7533. The light-emiting diode is of the type Siemens LD 242 if the above indicated values for R1, R2 and R3 are used, but the led can be of another type as well.

What is claimed is:

1. A bias control circuit for a light-emitting diode having compensation of the light output at changing temperature of the diode caused by its surroundings and current flowing through it, in which the light-emitting diode (led) is joined with a resistor (R3) in a first series circuit to which a fixed supply voltage is applied characterized in that a further series circuit of two further resistors (R1, R2) is connected in parallel across the resistor (R3) in the first series circuit and that a differential amplifier (A1) is provided, the one and the other input of the amplifier being connected respectively to the junction of the two further resistors and to a setting voltage (Vi), and the output of the amplifier being connected to a control means (Tr1) joined in series with the first series circuit to maintain constant the intensity of light emitted from the led despite changes in temperature.

2. A bias control circuit according to claim 1, characterized in that the two further resistors (R1, R2) in the further series circuit have substantially different values, the smaller resistor being connected to the led.

3. A bias control circuit according to claim 1, characterized in that the other input of the differential amplifier (A1), for an automatic bias control of the led when the fixed supply voltage is switched on or when the led is removed from the circuit and is reinstated, is connected to a step generator (1) supplying a step voltage at its output, and that a trigger means (A3) is provided, the one input of the trigger means being connected to said resistor (R3) in the first series circuit, the other input of the trigger means being connected to a reference voltage and the output of the trigger means being connected to an enable input (E) of the step generator, so that upon attaining the bias of the led determined by the reference voltage, the enabling signal is removed and the step generator is maintained in the attained position.

4. A bias control circuit according to claim 3, characterized in that a conversion means (A2), connected to the resistor (R3) in the first series circuit, is provided so that, when the fixed supply voltage is switched on and/or when the led has been removed, the higher voltage present in the first series circuit is derived and is supplied as reset voltage to a reset input (R) of the step generator.

5. A bias control circuit according to claim 3 or 4, characterized in that the step generator (1) consists of a clock circuit (2), a binary counter (3) and a digital-to-analog converter (4).

6. A bias control circuit according to claim 5, characterized in that for a light-modulating operation of the led, the other output of the differential amplifier (A1) is connected via a separating means (D1) to the pulsatile output signal of the clock circuit (2).

7. A bias control circuit according to claim 6, characterized in that a switching means (Tr2) is joined between the junction of the led and resistor (R3) in the first series circuit on one side and the smaller resistor (R2) of the two further resistors on the other side, the switching means including a switching input connected to the inverted, pulsatile output signal of the clock circuit (2), said smaller resistor at said other side of the switching means being connected also to a storing capacitor (C1).

8. A bias control circuit according to one of the preceding claims, characterized in that the control means (Tr1) is a transistor, that the differential amplifier (A1) and the conversion means (A2) are operational amplifiers, that the trigger means (A3) is an operational amplifier having Schmitt-effect, that the separating means (D1) is a diode and that the switching means (Tr2) is a transistor.

* * * * *